United States Patent [19]

Weaver et al.

[11] Patent Number: 5,453,482
[45] Date of Patent: Sep. 26, 1995

[54] PROCESS FOR PREPARING ARYLSULFONYL HALIDES

[75] Inventors: Max A. Weaver; William W. Parham; James J. Krutak; Kim S. Chamberlin, all of Kingsport, Tenn.

[73] Assignee: Eastman Chemical Company, Kingsport, Tenn.

[21] Appl. No.: 210,785

[22] Filed: Mar. 18, 1994

Related U.S. Application Data

[63] Continuation-in-part of Ser. No. 116,435, Sep. 3, 1993, abandoned.

[51] Int. Cl.$^6$ ............................ C08G 8/02; C08G 75/00
[52] U.S. Cl. .................... 528/172; 528/125; 528/126; 528/174; 528/220; 528/228; 528/272; 528/288; 528/289; 528/290; 528/295; 528/308; 525/535; 525/537; 525/540; 540/131
[58] Field of Search ............................ 540/131; 528/125, 528/172, 174, 220, 228, 272, 288, 289, 290, 295, 308, 126; 525/537, 540, 535

[56] References Cited

U.S. PATENT DOCUMENTS

| | | | |
|---|---|---|---|
| 2,731,476 | 1/1956 | Peter et al. | 260/371 |
| 3,299,103 | 1/1967 | Maler | 260/373 |
| 3,857,855 | 12/1974 | Idelson | 540/131 |
| 3,888,875 | 6/1975 | Bader et al. | 540/131 |
| 3,888,876 | 6/1975 | Bader et al. | 540/131 |
| 4,403,092 | 9/1983 | Davis et al. | 528/290 |
| 4,740,581 | 4/1988 | Pruett et al. | 528/289 |
| 5,032,670 | 7/1991 | Parham et al. | 528/220 |
| 5,102,980 | 4/1992 | Krutak et al. | 528/272 |

FOREIGN PATENT DOCUMENTS 0289952  11/1988  European Pat. Off.

OTHER PUBLICATIONS

Romeo B. Wagner and Harry D. Zook, "Synthetic Organic Chemistry," John Wiley & Sons, New York, pp. 821-826 (1953).
C. M. Suter, "The Organic Chemistry of Sulfur," John Wiley & Sons, Inc., New York (1944).
R. C. Fuson, "Reactions of Organic Compounds," John Wiley & Sons, Inc., New York, pp. 42-43 (1962).

*Primary Examiner*—Paul R. Michl
*Assistant Examiner*—P. Hampton-Hightower
*Attorney, Agent, or Firm*—Bernard J. Graves, Jr.; Harry J. Gwinnell

[57] ABSTRACT

Provided is a new process useful for preparing arylsulfonyl halides, which comprises the addition or drowning of halosulfonation reaction products, produced by the reaction of aromatic compounds (arenes), with excess halosulfonic acid, into $C_3$–$C_6$ aliphatic ketones, preferably acetone, isopropyl alcohol, or mixtures thereof, instead of drowning into water as is known in the art of aromatic sulfonyl chloride preparation. Less heat of reaction is observed, thus making the drowning of the halosulfonation reaction mixture safer and more controllable. Further, less hydrogen chloride gas is evolved from the drowning mixture and generally more highly pure arylsulfonyl chlorides are produced.

25 Claims, No Drawings

PROCESS FOR PREPARING ARYLSULFONYL HALIDES

CROSS REFERENCE TO RELATED APPLICATION

This application is a continuation-in-part of U.S. patent application Ser. No. 08/116,435, filed Sep. 3, 1993, now abandoned, incorporated herein by reference.

FIELD OF THE INVENTION

This invention belongs to the field of synthetic organic chemistry. In particular, it relates to an improved process for the synthesis of arylsulfonyl halides.

BACKGROUND OF THE INVENTION

It is well known that one may prepare arylsulfonyl chlorides by replacement of a hydrogen atom on an aromatic compound by reacting the aromatic compound with chlorosulfonic acid. (See, for example, Romeo B. Wagner and Harry D. Zook, "Synthetic Organic Chemistry", John Wiley & Sons, New York, pp. 821–826 (1953); C. M. Suter, "The Organic Chemistry of Sulfur" John Wiley & Sons, Inc., New York (1944); R. C. Fuson, "Reactions of Organic Compounds" John Wiley & Sons, Inc., New York, pp. 42–43 (1962); U.S. Pat. No. 2,731,476; U.S. Pat. No. 3,299,103; U.S. Pat. No. 4,403,092; and U.S. Pat. No. 5,102,980.)

In general, the chlorosulfonation reaction has been carried out by using excess chlorosulfonic acid as the solvent and the aromatic sulfonyl chlorides have been isolated by drowning the chlorosulfonation reaction mixtures into ice or an ice/Water mixture. This is a difficult procedure because of the violent exothermic reaction of the excess chlorosulfonic acid with water, accompanied by copious quantities of hydrogen chloride and sulfur dioxide gas evolution. Further, on prolonged contact with the water, hydrolysis of the arylsulfonyl chloride may occur. Attempts to remove the water by drying may also result in hydrolysis. The resulting hydrolysis products, the arylsulfonic acids, are difficult to remove and may render the thus impure arylsulfonyl chlorides useless. For example, when the arylsulfonyl chlorides are used as in the functionalization of colored compounds to produce colored sulfonamides, which contain reactive polyester groups such as hydroxy, carboxy, carboxylic esters, etc., and which may be incorporated into the polyester by copolymerization with the diacid and/or diol during the polycondensation reaction (see, for example, U.S. Pat. No. 4,403,092, incorporated herein by reference), any remaining colored arylsulfonic acid may not be covalently bound to the polymer and may result in problems such as extractability, migration, etc. Further, we have observed that high levels of colored arylsulfonic acids present in the colored functionalized arylsulfonamides cause problems in the polymerization reaction in that only low molecular weight polymers are produced and high levels of diethylene glycol are observed when ethylene glycol is the selected diol, which is the preferred diol for most polyesters.

Finally, EP 0,289,952 describes the reaction of acetone with chlorosulfonic acid, preferably in the presence of a solvent, such as methylene chloride, for the reactants. No mention is made of utilizing ketones as a drowning medium for the chlorosulfonation reaction solutions such as described herein.

SUMMARY OF THE INVENTION

It has been found that high purity arylsulfonyl halides are conveniently prepared by (a) contacting an aromatic compound (arene), capable of undergoing electrophilic attack, with a halosulfonic acid and (b) adding the halosulfonation reaction mixture of step (a) to a $C_3$–$C_6$ aliphatic ketone, a mixture of $C_3$–$C_6$ aliphatic ketones, a $C_3$–$C_6$ aliphatic ketone/isopropyl alcohol blend, or isopropyl alcohol, with stirring and cooling to precipitate the solid arylsulfonyl halide thus produced.

DETAILED DESCRIPTION OF THE INVENTION

The present invention provides a process for preparing an arylsulfonyl halide of the formula $$R-(SO_2-X)_n,$$

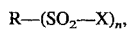

wherein X is halo, n is an interger of from 1 to 4, and R is an aryl group, which comprises reacting an aromatic compound of the formula R—H with a halosulfonic acid, followed by treatment with a molar excess of a $C_3$–$C_6$ aliphatic ketone. In a further aspect of the present invention, the process can utilize a mixture of a $C_3$–$C_6$ aliphatic ketone and isopropyl alcohol or isopropyl alcohol alone. In this regard, as a preferred embodiment of the present invention, the drowning solution of the $C_3$–$C_6$ aliphatic ketone will contain at least 25% by weight of isopropyl alcohol.

The invention herein provides a convenient method for preparing high purity arylsulfonyl halides, especially arylsulfonyl chlorides. Depending on the starting aromatic compound (arene) from which the arylsulfonyl halides are derived, they are useful as colorants, pharmaceuticals, agricultural products, etc.

This invention utilizes a $C_3$–$C_6$ aliphatic ketone, preferably acetone, a mixture of $C_3$–$C_6$ aliphatic ketones, a $C_3$–$C_6$ aliphatic ketone/isopropyl alcohol mixture, or isopropyl alcohol, instead of water as the drowning medium for the halosulfonation reaction solution and thereby eliminates many of the problems encountered with the known process.

The halosulfonation reaction is preferably carried out at temperatures of about 0° C. to about 100° C., most preferably at about room temperature (i.e., ~25° C.). Preferably, the arene is added to excess halosulfonic acid with stirring and external cooling, if needed, at about 20°–30° C. If required, the reaction mixture is heated to complete the halosulfonation reaction. For each active hydrogen site (i.e., a site capable of undergoing electrophilic attack) desired in the arene, at least two equivalents of halosulfonic acid are generally required, first to bring about sulfonation of the arene and secondly to convert the arylsulfonic acid thus produced to the arylsulfonyl halide. Of course, if there are multiple sites capable of undergoing electrophilic attack in the arene, then multiple sulfonyl halide groups may be introduced. The active site(s) may be on an aromatic nucleus or on one or more pendent aryl groups connected by a divalent linking group to an aromatic nucleus. It is also preferable to use several fold molar excess of halosulfonic acid to the arene to achieve solution of the arene and the complete conversion of the intermediate arylsulfonic acid compound to the desired arylsulfonyl halide. Preferred molar excesses of halosulfonic acid to the moles of arene to be halosulfonated range from about 10/1 to about 50/1 with about 20/1 to about 40/1 being most preferred, depending on the solubility of the arene in the halosulfonic acid, the number of active sites and the rate of reaction of the arene with the halosulfonic acid. In the above process, the halosulfonation is preferably a chlorosulfonation.

In the practice of this invention, arylsulfonyl halides are isolated from the halosulfonation reaction solutions as described above, by drowning (i.e., adding) said solutions to a $C_3$–$C_6$ aliphatic ketone, a mixture of $C_3$–$C_6$ aliphatic ketones, a $C_3$–$C_6$ aliphatic ketone/isopropyl alcohol, or isopropyl alcohol, to produce solid arylsulfonyl halides, which are collected by filtration of the drowning mixtures to collect the desired arylsulfonyl halides in a normal work-up. The solid arylsulfonyl halides may be purified by washing or reslurrying with the same or different $C_3$–$C_6$ aliphatic ketone, a mixture of $C_3$–$C_6$ aliphatic ketones, lower alkanols, or another inert solvent which does not react with the arylsulfonyl halides. Typical $C_3$–$C_6$ aliphatic ketones include 2-propanone (acetone), 2-butanone (methyl ethyl ketone), 2-pentanone, 3-pentanone, 3-methyl-2-butanone, 4-methyl-2-pentanone, etc. Acetone is preferred as the ketone.

The amount of $C_3$–$C_6$ aliphatic ketone, $C_3$–$C_6$ aliphatic ketone mixture, $C_3$–$C_6$ aliphatic ketone/isopropyl alcohol, or isopropyl alcohol used for the drowning of the halosulfonation reaction solutions may vary considerably, but preferably the desired ratio of the drowning medium to the volume of the chlorosulfonic acid used in the reaction varies between about 2/1 to 20/1 (v/v).

The arene substrate of the formula R—H, can be any aromatic compound which has an active hydrogen, i.e., a site capable of electrophilic substitution, as in a halosulfonation of, for example, benzene.

Examples of such arene compounds include carbocyclic and heterocyclic aryl compounds containing up to fifty carbons, e.g., benzene, naphthyl, naphthalene, anthracene, anthrapyridone, anthraquinone, acridone, phthalocyanine, naphthalocyanine, phenanthrene, and such compounds substituted with one or two groups selected from $C_1$–$C_4$-alkyl, $C_1$–$C_4$ alkoxy, $C_1$–$C_4$-alkoxycarbonyl, arylamino, aryloxy, arylthio, $C_1$–$C_4$-alkanoyloxy, $C_1$–$C_4$-alkanoylamino, halogen, cyano, hydroxy, nitro, $C_1$–$C_4$-alkylsulfonyl, $C_1$–$C_4$-alkylthio, —$SO_2N(R_1)R_2$; —$CON(R_1)R_2$; —$N(R_1)R_2$; wherein $R_1$ and $R_2$ are independently selected from hydrogen, $C_1$–$C_4$ alkyl, aryl, $C_3$–$C_8$ cycloalkyl and further provided that each $C_1$–$C_4$ alkyl group in these definitions may contain one or more substituents selected from $C_1$–$C_4$ alkoxy, $C_1$–$C_4$ alkylthio, $C_1$–$C_4$ alkylsulfonyl, aryloxy, arylthio, arylsulfonyl, halogen, or $C_3$–$C_8$-cycloalkyl, etc. In defining the groups which may be available as substituents on the arene moiety, the term aryl is used to include phenyl and naphthyl and such groups substituted by $C_1$–$C_4$ alkyl, $C_1$–$C_4$ alkoxy, halogen, $C_1$–$C_4$ alkoxycarbonyl, $C_1$–$C_4$ alkanoylamino, cyano, and nitro. Typical useful arenes of the anthraquinone class are disclosed in U.S. Pat. No. 4,403,082 and U.S. Pat. No. 3,299,103; typical useful arenes of the anthrapyridone class are disclosed in U.S. Pat. No. 4,740,581 and U.S. Pat. No. 4,745,178, incorporated herein by reference.

Other suitable arene compounds include 5 or 6-membered heterocyclic aromatic rings containing one oxygen atom, and/or one sulfur atom, and/or up to three nitrogen atoms, said heterocyclic arene rings optionally fused to one or two phenyl rings or another 5 or 6-membered heteroaryl ring. Examples of such ring systems include thiophene, furan, pyrrole, imidazole, pyrazole, thiazole, isothiazole, oxazole, isoxazole, triazole, thiadiazole, oxadiazole, tetrazole, thiatriazole, oxatriazole, pyridine, pyrimidine, pyrazine, pyridazine, thiazine, oxazine, thiadiazine, oxadiazine, dithiazine, dioxazine, oxathiazine, tetrazine, thiatriazine, oxatriazine, dithiadiazine, imidazoline, dihydropyrimide, tetrahydropyrimide, tetrazolo-[1,5-b]-pyridazine and purine, benzoxazole, benzothiazole, benzimidazole, indole, and the like and such rings substituted with one or two substituents listed above in the examples of the term "arene".

The arene may be a single or multiple aromatic ring system, either condensed or combined by linking groups such as oxygen, sulfur, amino, sulfone, $C_1$–$C_4$-alkyene, $C_1$–$C_4$-alkyleneoxy, $C_1$–$C_4$ alkylenethio, $C_1$–$C_4$-alkylenesulfonyl, and the like.

A preferred arene consists of an anthraquinone or anthrapyridine residue linked to one or more benzene rings via oxygen, sulfur, amino, etc., with the arene being optionally substituted with the groups mentioned above.

In an especially preferred embodiment of the present invention, R—H is selected from the group consisting of

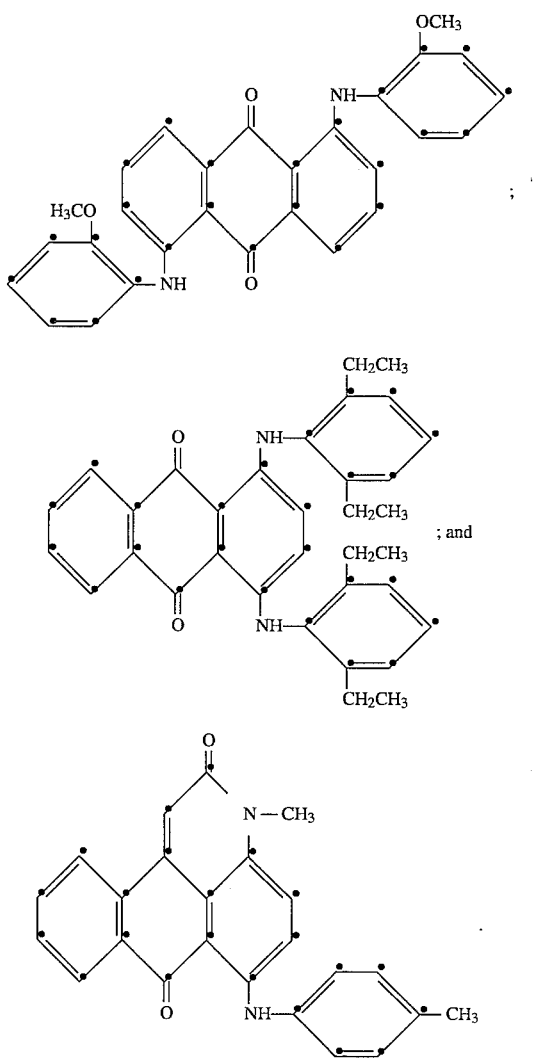

In this regard, the process of the present invention is especially useful for introducing chlorosulfonyl groups into the above compounds to provide compounds of the formula

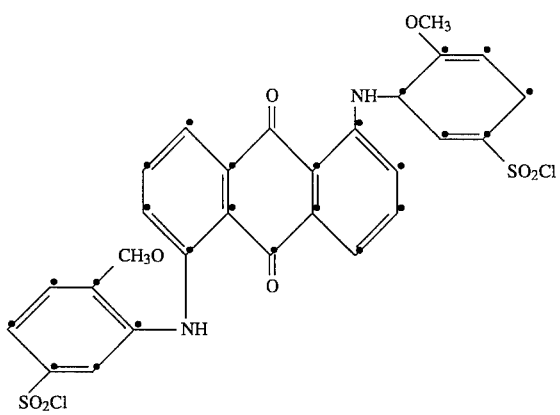
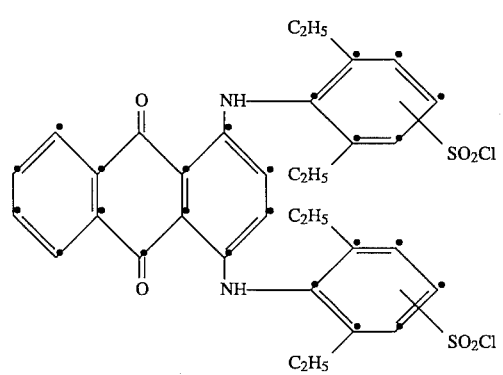
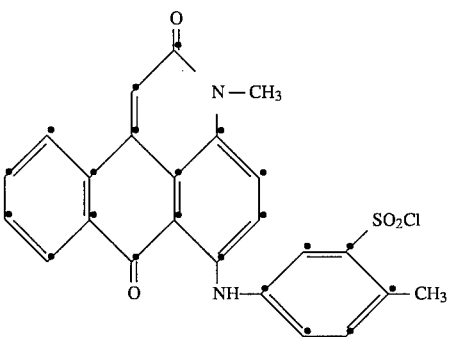
The above compounds are useful as toners in polyesters and are described in copending application U.S. Ser. No. 08/116,419, filed on Sep. 3, 1993, U.S. Pat. No. 5,372,864, entitled "Toners for Polyesters", incorporated herein by reference.
Further preferred compounds of the formula R—H include the following compounds which are useful as infrared/visible light absorbers:
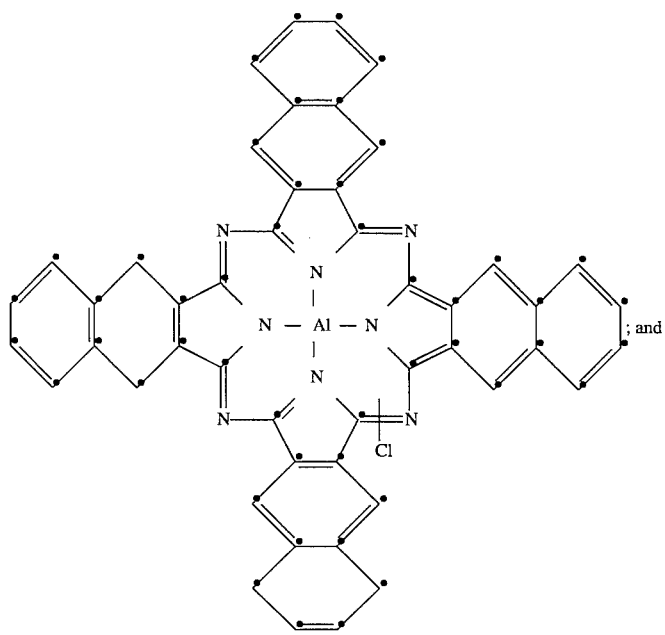
; and

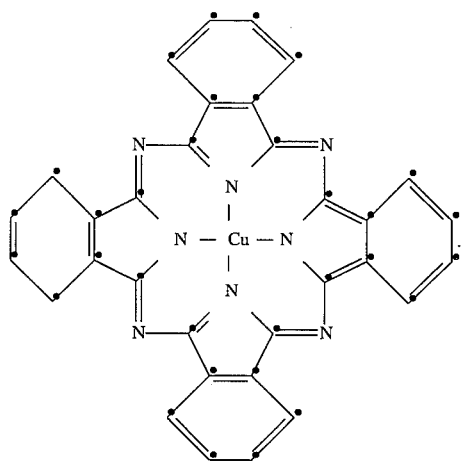

When compared to the known method of isolating arylsulfonyl halides from halosulfonation reactions involving large excesses of chlorosulfonic acid by drowning in water or water/ice, the method of the present invention has the advantages of (1) the addition of the chlorosulfonation reaction mixture to the drowning medium is not as exothermic and uncontrollable as the contacting of chlorosulfonic acid with water or water/ice mixture, (2) the evolution of hydrogen chloride and sulfur dioxide gases from the drowning mixture is greatly minimized, and (3) the arylsulfonyl chloride may be utilized without isolation in further reactions or may be conveniently dried without being in contact with water which may cause problems with hydrolysis.

The following examples illustrate further the practice of the invention.

EXPERIMENTAL SECTION

Example 1

To chlorosulfonic acid (25.0 mL) was added 1,5-bis(2-anisidino)anthraquinone (4.50 g, 0.01 m) with stirring at <35° C. After complete addition, the reaction solution was stirred at about 25° C. for 3.0 hours and then added gradually to acetone (400 mL) with stirring and with external cooling to keep the temperature of the drowning mixture at <20° C. The solid di-sulfonyl chloride compound was collected by filtration, washed well with acetone and dried in air. The yield of product was 5.64 g (87.0% of the theoretical yield). Field desorption mass spectrometry (FDMS) gave a molecular ion mass of 646 from a tetrahydrofuran solution which supports the following desired structure:

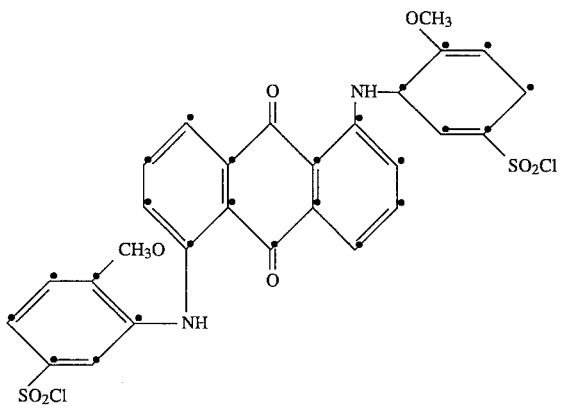

The above red product was useful for reacting with amines containing polyester reactive groups to produce functionalized colorants which are useful for producing colored polyester compositions (U.S. Pat. No. 4,403,092).

Example 2

To chlorosulfonic acid (400 mL) was added 1,4-bis(2,6-diethylanilino)anthraquinone (50.0 g, 0.10 m) portionwise with stirring at <45° C. After being stirred overnight at room temperature, the reaction mixture was added with stirring to acetone (1.0 L), keeping the temperature below about 15° C. The solid thus produced was collected by filtration, washed with acetone (cooled to about 0° C.) and then dried in air. The yield of bright blue product was 47.3 g (67.8% of the theoretical yield). FDMS from a tetrahydrofuran solution of the product showed a molecular ion mass of 698 which supports the following desired structure:

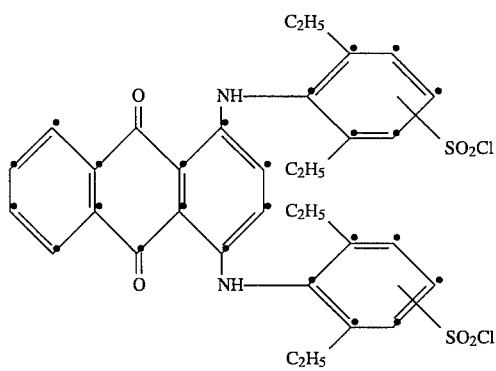

Example 3

To chlorosulfonic acid (15.0 mL) was added 3-methyl-6-p-toluidino-3H-dibenz(f,ij) isoquinoline- 2,7-dione (5.0 g, 0.0137 m) portionwise allowing the temperature to rise to about 35° C. The reaction solution was stirred at room temperature for 2.5 hours and then added gradually to acetone (100 mL) at <15° C. The product was collected by filtration, washed with acetone and dried in air to give presumably the following product in essentially quantitative yield.

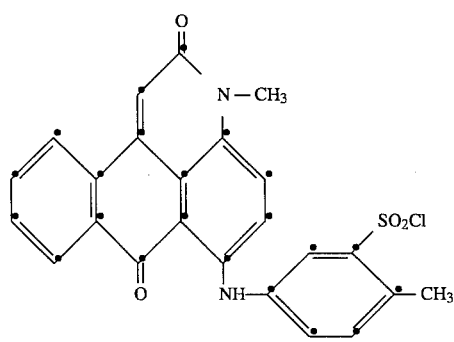

The product when dissolved in N,N-dimethylformamide produced a bright red color consistent with the proposed structure.

Example 4

50:50 Isopropyl Alcohol:Acetone by Volume

To chlorosulfonic acid (150.0 mL was added 1,5-bis(2-anisidino)anthraquinone (45.1 g, 0.10M) at less than 45° C. with good stirring, which was continued for four hours without any heat being applied. The reaction mixture was then drowned into a mixture of acetone (500 mL) and isopropyl alcohol (500 mL), keeping the temperature at less than 25° C. After being collected by filtration, the red anthraquinone di-sulfonyl chloride product was washed with two 250 mL portions of isopropyl alcohol and then air dried. The yield of product which had the same structure as product of Example 1 was 62.3 g (96.1% of the theoretical yield).

Example 5

80:20 Isopropyl Alcohol:Acetone by Volume

Example 4 was repeated except that the chlorosulfonation reaction mixture was drowned into a mixture of isopropyl alcohol (800 mL) and acetone (200 mL). The product was collected and washed with two 250 mL portions of isopropyl alcohol and dried (64.1 g, 99.0% of the theoretical yield).

Example 6

100% Isopropyl Alcohol

To chlorosulfonic acid (150 mL) was added portionwise with stirring 1,5-bis(2-anisidino)-anthraquinone (45.1 g, 0.10M) keeping the temperature at less than 45° C. The reaction mixture was stirred overnight, allowing the temperature to adjust to room temperature, and then drowned into isopropyl alcohol (1.0 L) at 0°– 10° C. After being stirred for 30 minutes at 0°–10° C., the reaction mixture was filtered by vacuum. The solid product which had the same structure as the product of Example 1 was washed with isopropyl alcohol (500 mL) and then air dried. Essentially a quantitative yield of product was obtained.

Example 7

100% Isopropyl Alcohol

To chlorosulfonic acid (150 mL) was added 1,4-bis(2,6-diethylanilino) anthraquinone (50.2 g, 0.10M) portionwise with stirring at less than 45° C. The reaction mixture was stirred overnight allowing the temperature to adjust to room temperature and then drowned into isopropyl alcohol (1.0 L) with stirring at 0°–10° C. After stirring the drowning mixture for 30 minutes at 0°–10° C., the blue anthraquinone di-sulfonyl chloride product, which had the same structure as the product of Example 2, was collected by filtration, washed with isopropyl alcohol (500 mL) and dried in air (yield 68.3 g, 97.8% of the theoretical yield).

We claim:

1. A process for preparing an arylsulfonyl halide of the formula $$R—(SO_2—X)_n,$$

wherein X is halo, n is an integer of from 1 to 4, and R is an aryl group, which comprises reacting an aromatic compound of the formula R—H with a halosulfonic acid, followed by treatment with a molar excess of a $C_3$–$C_6$ aliphatic ketone.

2. The process of claim 1, wherein X is chloro.
3. The process of claim 1, wherein X is bromo.
4. The process of claim 1, wherein R—H is an anthraquinone residue linked to at least one benzene ring by sulfur, oxygen or amino.
5. The process of claim 1, wherein R—H is an anthrapyridone residue linked to at least one benzene ring by sulfur, oxygen or amino.
6. The process of claim 1, wherein R—H is selected from the group consisting of

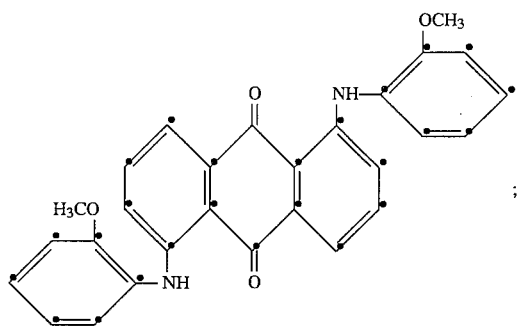
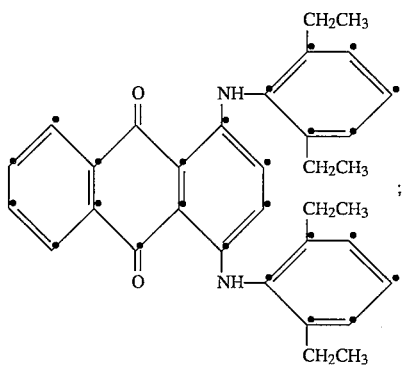
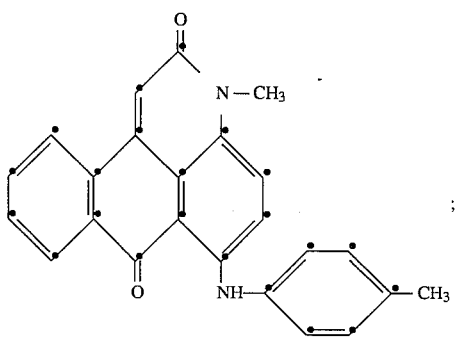
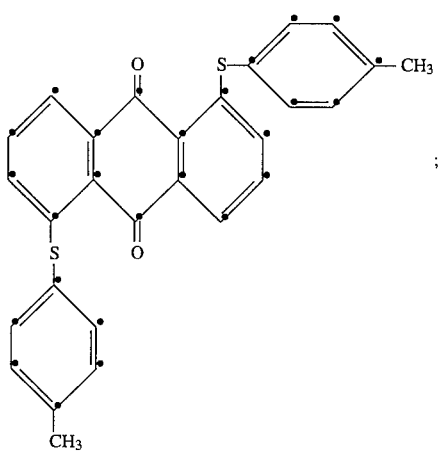

-continued
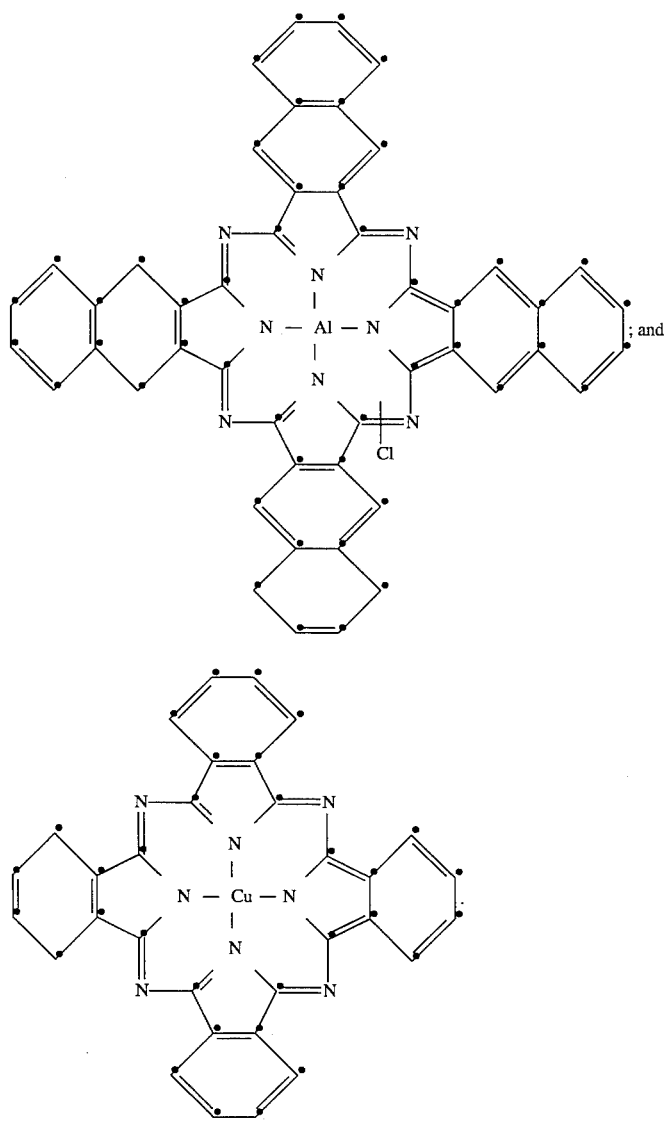
7. The process of claim 1, wherein R—H is
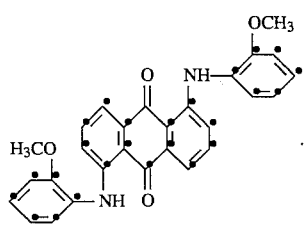
8. The process of claim 1, wherein R—H is
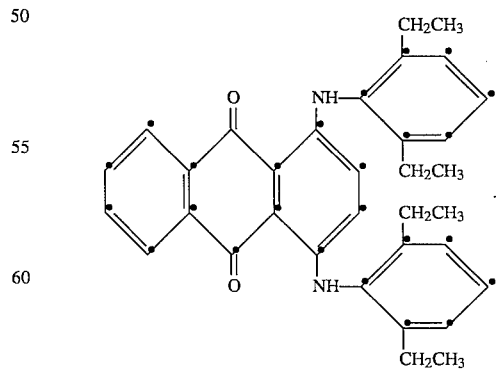

9. The process of claim 1, wherein R—H is

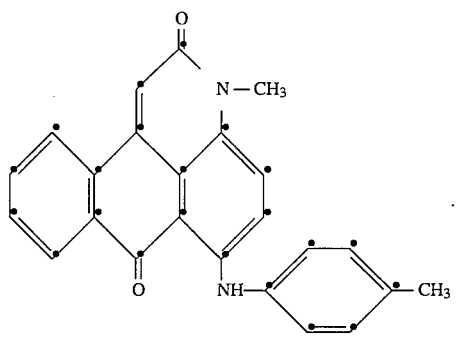

10. The process of claim 1, wherein R—H is

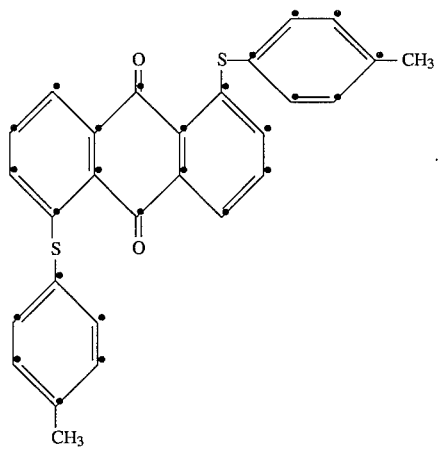

11. The process of claim 1, wherein R—H is

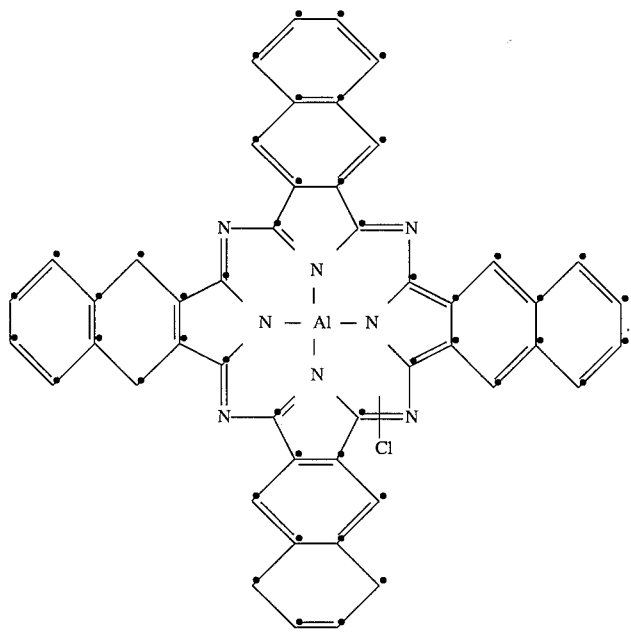

12. The process of claim 1, wherein R—H is

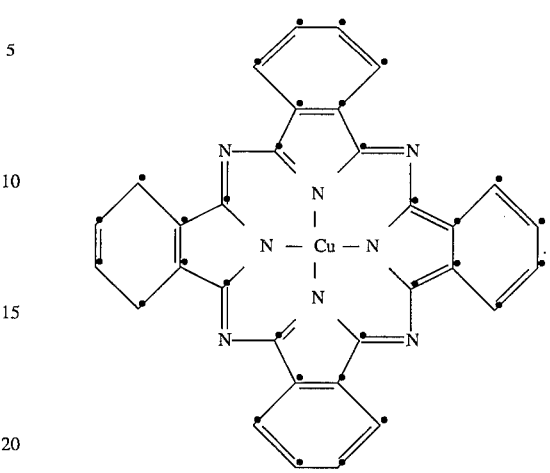

13. A process for preparing an arylsulfonyl halide of the formula $$R-(SO_2-X)_n,$$

wherein X is halo, n is an integer of from 1 to 4, and R is an aryl group, which comprises reacting an aromatic compound of the formula R—H with a halosulfonic acid, followed by treatment with a molar excess of isopropyl alcohol or a mixture of isopropyl alcohol and a $C_3$-$C_6$ aliphatic ketone.

14. The process of claim 13, wherein X is chloro.

15. The process of claim 13, wherein X is bromo.

16. The process of claim 13, wherein R—H is selected from the group consisting of

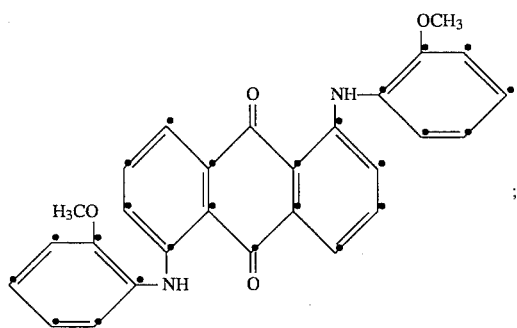
;
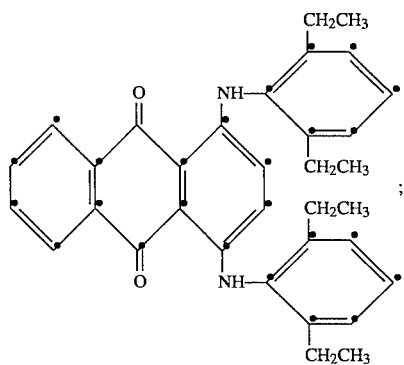
;
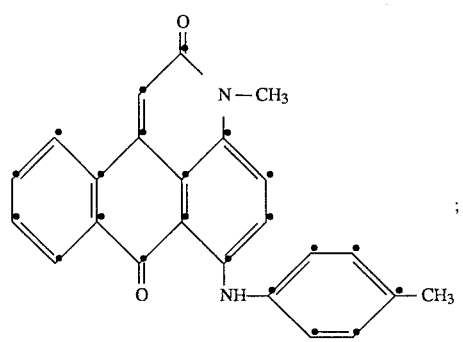
;
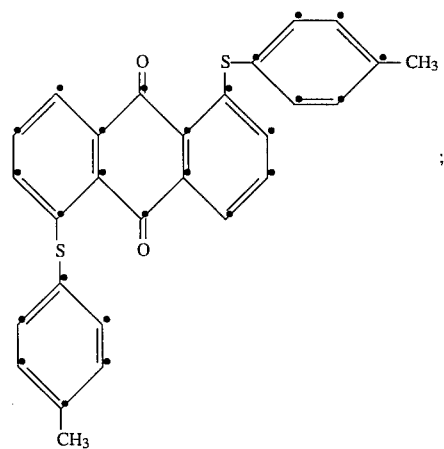
;

-continued
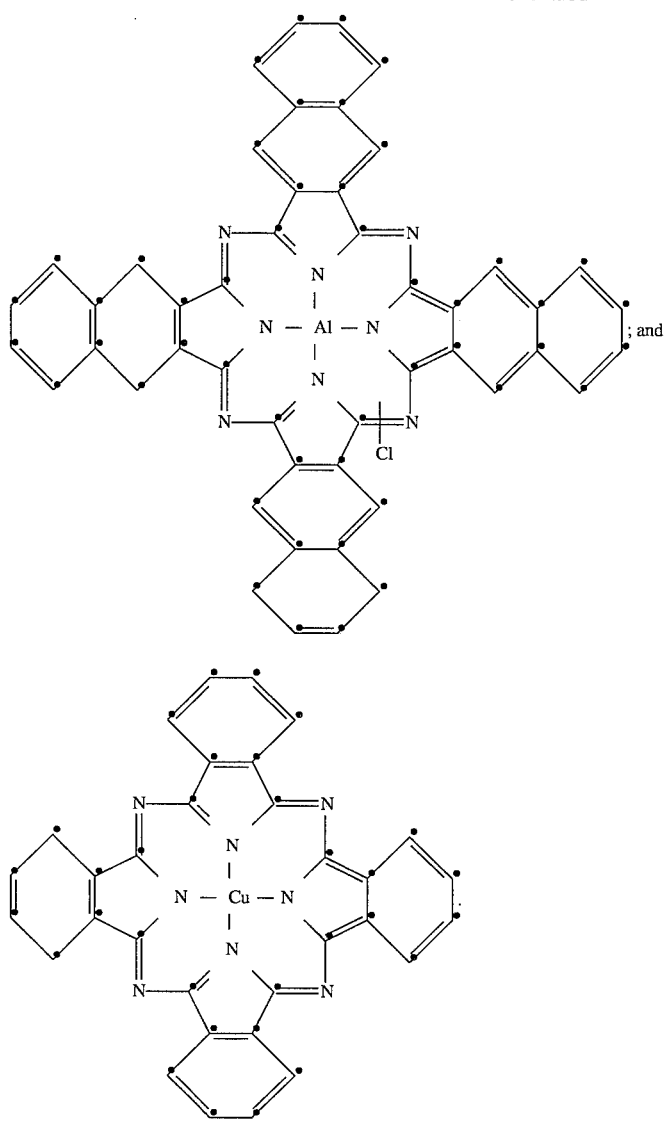
; and
17. The process of claim 13, wherein R—H is
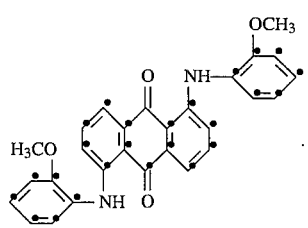
18. The process of claim 13, wherein R—H is
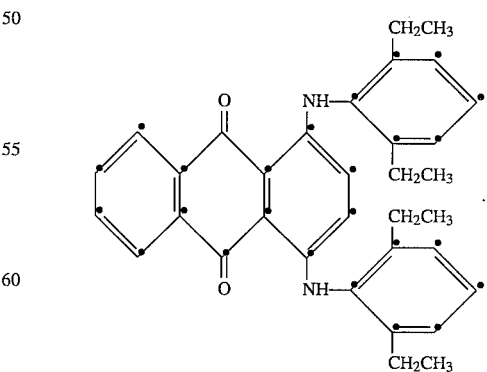

19. The process of claim 13, wherein R—H is

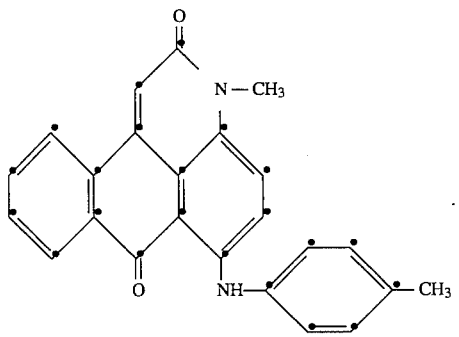

20. The process of claim 13, wherein R—H is

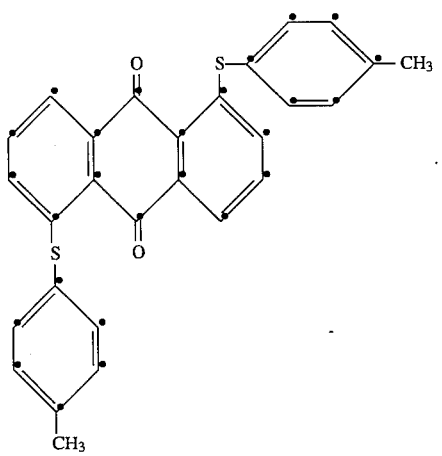

21. The process of claim 13, wherein R—H is

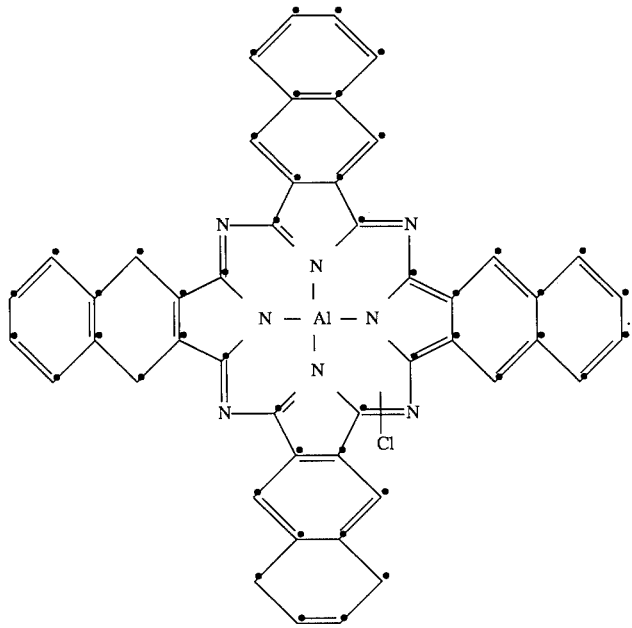

22. The process of claim 13, wherein R—H is

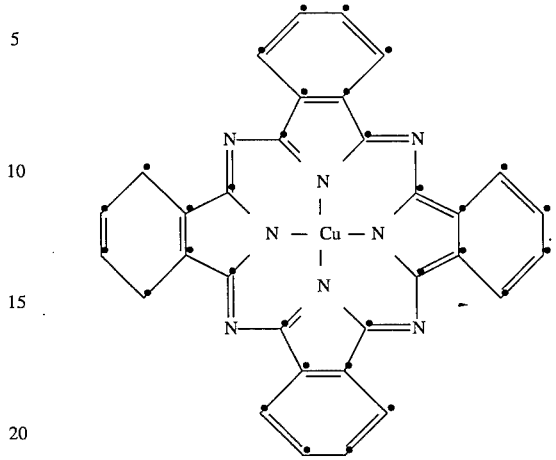

23. The process of claim 13, wherein the mixture of isopropanol and a $C_3$–$C_6$ aliphatic ketone contains at least 25% isopropyl alcohol by weight.

24. The process of claim 13, wherein the $C_3$–$C_6$ aliphatic ketone is acetone.

25. The process of claim 13, wherein isopropyl alcohol is utilized alone.

* * * * *